(12) United States Patent
Tjhang et al.

(10) Patent No.: US 9,611,735 B2
(45) Date of Patent: Apr. 4, 2017

(54) IMAGE-BASED MEASUREMENT OF A FLUID

(71) Applicant: Schlumberger Technology Corporation, Sugar land, TX (US)

(72) Inventors: Theodorus Tjhang, Kita-ku (JP); Tsutomu Yamate, Yokohama (JP); Yutaka Imasato, Chiba (JP); Akira Kamiya, Sagamihara (JP); Kazumasa Kanayama, Hachioji (JP)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 14/540,015

(22) Filed: Nov. 12, 2014

(65) Prior Publication Data

US 2015/0138557 A1 May 21, 2015

Related U.S. Application Data

(60) Provisional application No. 61/905,001, filed on Nov. 15, 2013.

(51) Int. Cl.
*E21B 49/08* (2006.01)
*E21B 47/12* (2012.01)
*G01N 21/59* (2006.01)
*G01N 15/06* (2006.01)
*G01N 21/51* (2006.01)

(52) U.S. Cl.
CPC ........... *E21B 47/123* (2013.01); *G01N 15/06* (2013.01); *G01N 21/51* (2013.01); *G01N 2015/0693* (2013.01)

(58) Field of Classification Search
CPC ............... G01N 21/51; G01N 15/06; G01N 2015/0693; G01N 2001/06113; E21B 47/123; E21B 49/087
USPC .......... 356/432–437, 445, 246, 241.1–241.6; 250/559.19, 559.22, 559.24
See application file for complete search history.

(56) References Cited

U.S. PATENT DOCUMENTS

| | | | | |
|---|---|---|---|---|
| 4,355,904 A | * | 10/1982 | Balasubramanian | G01C 3/24 356/16 |
| 4,967,092 A | * | 10/1990 | Fraignier | G01B 11/24 250/559.07 |
| 5,895,927 A | * | 4/1999 | Brown | G01B 11/12 250/559.19 |
| 7,164,476 B2 | * | 1/2007 | Shima | G01N 21/954 250/559.07 |
| 7,557,914 B2 | * | 7/2009 | Thompson | G01B 11/02 356/241.1 |

(Continued)

OTHER PUBLICATIONS

"Inflow Turbidity / Color Analysis / Percent Solids Measurement Systems," Canty Process Technology website at http://www.jmcanty.com/itemDetail.aspx?itemId=TA10591-1.

(Continued)

*Primary Examiner* — Sang Nguyen

(57) ABSTRACT

An imaging-based measurement apparatus includes a light source, and at least one optical element for positioning in a flow conduit, the at least one optical element being part of a light path for light emitted by the light source, where light along the light path passes through a portion of fluid flowing in the flow conduit. An image sensor detects the light and measures content of the portion of the fluid.

16 Claims, 8 Drawing Sheets

(56) References Cited

U.S. PATENT DOCUMENTS

| | | | | |
|---|---|---|---|---|
| 8,328,731 | B2* | 12/2012 | Hessel | A61B 5/0062 |
| | | | | 181/129 |
| 8,334,971 | B2* | 12/2012 | Keller | G01N 21/954 |
| | | | | 356/237.2 |
| 8,336,630 | B2 | 12/2012 | Kerr | |
| 8,873,034 | B2* | 10/2014 | Lin | A61B 5/0066 |
| | | | | 356/246 |
| 2012/0076364 | A1 | 3/2012 | Tjhang et al. | |
| 2013/0265409 | A1 | 10/2013 | Tjhang et al. | |

OTHER PUBLICATIONS

Yoshihiro Watanabe, Takashi Komuro, Shingo Kagami, Masatoshi Ishikawa, Real-time Visual Measurements using High-speed Vision, Optics East (Philadelphia Oct. 28, 2004) /Machine Vision and its Optomechatronic Applications, Proceedings of SPIE vol. 5603, pp. 234-242.

R.J. Adrian "Twenty Years of Particle Image Velocimetry." Experiments in Fluids 2005, vol. 39, Issue 2, (11 pgs).

Chunxiao Tang et al. "Double-Wavelength Digital Particle Image Velocimetry." Control, Automation and Systems Engineering (Case), 2011, (4 pgs).

\* cited by examiner

IMAGE-BASED MEASUREMENT OF A FLUID

CROSS-REFERENCE TO RELATED APPLICATION

This application claims the benefit under 35 U.S.C. §119(e) of U.S. Provisional Application No. 61/905,001, entitled "Fluid Measurement System with Cleanable Subsurface Particle Detection and Method of Using Same," filed Nov. 15, 2013, which is hereby incorporated by reference.

BACKGROUND

Wells can be drilled into a subsurface formation to allow communication with one or more reservoirs in the subsurface formation. A production well is used to produce fluids from the reservoir(s). An injector well can be used to inject fluids into the reservoir(s).

SUMMARY

In general, according to some implementations, an imaging-based measurement apparatus includes a light source, and at least one optical element for positioning in a flow conduit, the at least one optical element being part of a light path for light emitted by the light source, where light along the light path passes through a portion of fluid flowing in the flow conduit. An image sensor detects the light and measures content of the portion of the fluid.

In general, according to further implementations, a system includes a tubular structure providing a flow conduit in which fluid is to flow, wherein the tubular structure comprises a transparent tubular insert connected between non-transparent tubular segments. A light source emit lights that passes through the transparent tubular insert, and an image sensor receives light passed through the transparent tubular insert and through a portion of the fluid.

In general, according to additional implementations, a method of sampling fluid includes connecting flowlines to a flow conduit that carries a flow of fluid, and actuating a flow control mechanism from a closed position to an open position to cause flow of a portion of the fluid through the flowlines, the portion of the fluid to pass through a measurement chamber. A light source is activated to emit light that passes through the measurement chamber, and an image sensor receives the light that passes through the measurement chamber to measure content of the portion of the fluid.

Other or additional features will become apparent from the following description, from the drawings, and from the claims.

DETAILED DESCRIPTION

Figure 1:
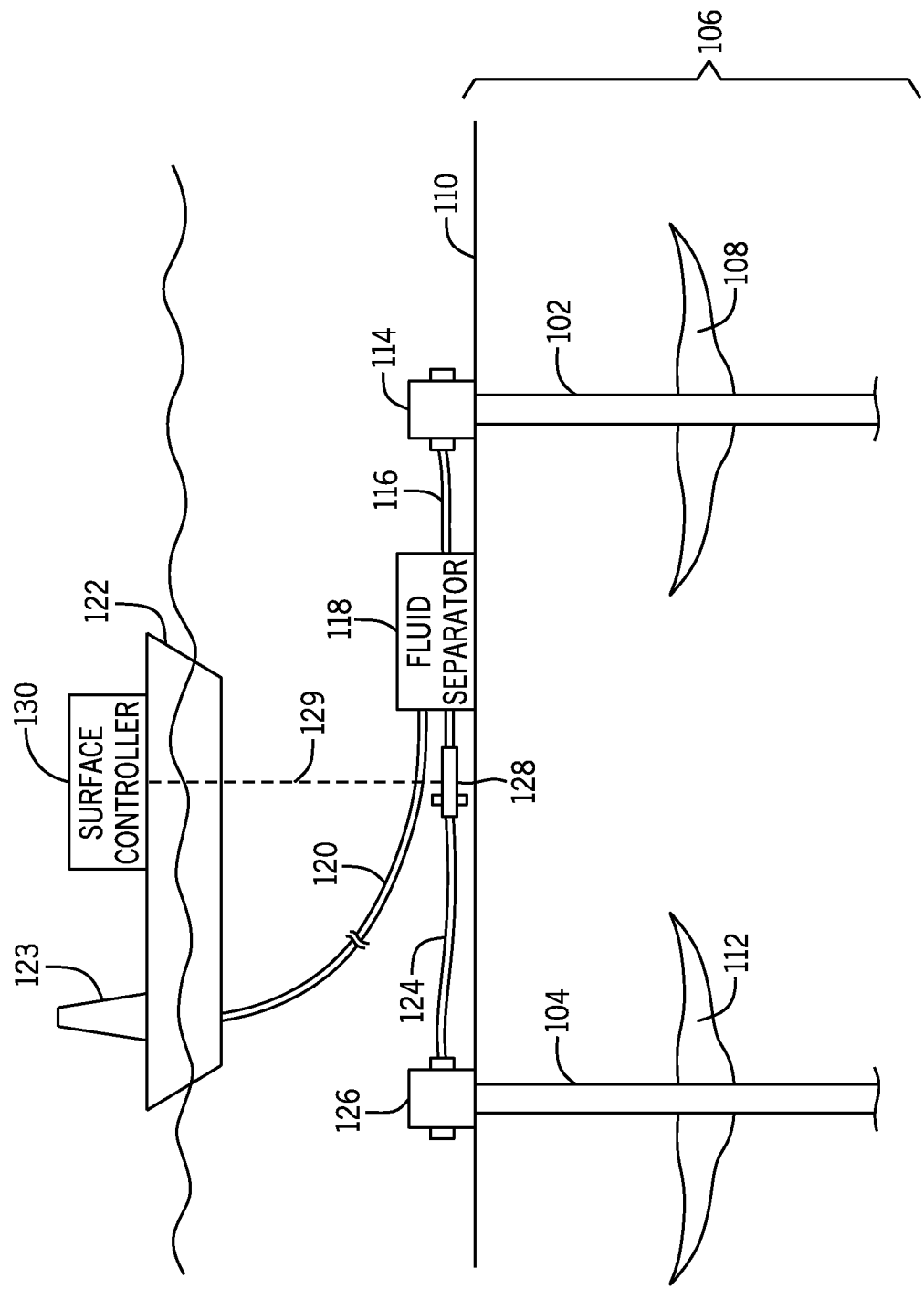
FIG. 1 is a schematic diagram of a subsea wellsite arrangement that includes a fluid measurement system according to some implementations.

FIG. 1 is a schematic diagram showing a subsea wellsite arrangement that includes a production well 102 and an injection well 104 that have been drilled into a subsurface formation 106. Although just one production well 102 and/or injection well 104 are depicted in FIG. 1, it is noted that there can be more than one production well and/or more than one injection well in other examples.

Also, although FIG. 1 shows techniques or mechanisms according to some implementations being used in a subsea context, it is noted that in other examples, techniques or mechanisms according to some implementations can be used with a land-based wellsite arrangement.

Even more generally, techniques or mechanisms according to some implementations can be applied to fluid measurements in other contexts unrelated to well production or injection.

The production well 102 is able to produce fluids (e.g. hydrocarbons such as oil and/or gas, or other types of fluids) from a reservoir 108 towards a surface, which in the example of FIG. 1 is a water bottom surface 110 (e.g., seafloor). The injector well 104 can be used to inject fluids into a reservoir 112. Although just one reservoir 108 and one reservoir 112 are depicted in association with the production well 102 and the injection well 104, respectively, it is noted that in other examples, the production well 102 can produce fluids from multiple reservoirs, and/or the injection well 104 can inject fluid into multiple reservoirs.

At the water bottom surface 110, wellhead equipment 114 is provided. Fluid produced from the reservoir 108 flows up through the production well 102 to the wellhead equipment 114. The production fluids pass through the wellhead equipment 114 to a flow conduit 116 that is attached to and in fluid communication with the wellhead equipment 114. The flow conduit 116 can include a pipe, a flowline, and so forth.

The fluid conduit 116 is further connected to and in fluid communication with a fluid separator 118, which receives fluid flow from the fluid conduit 116. The fluid separator 118 separates the received fluid flow into multiple separated fluid portions. In some examples, the fluid separator 118 is used for separating hydrocarbons from water that may be present in the fluid flow received from the flow conduit 116. The hydrocarbons can include oil and/or gas. The fluid separator 118 separates the fluid flow in the flow conduit 116 into (1) a first separated fluid portion that is provided to a production flow conduit 120, and (2) a second separated fluid portion that is provided to an injection flow conduit 124. Separation of a fluid flow into hydrocarbons and water can be based on the specific gravity difference between the hydrocarbons and the water.

Each of the flow conduits 120 and 124 can include a pipe, a flowline, and so forth. The injection flow conduit 120 runs from the fluid separator 118 to a surface marine vessel 122 (e.g. a sea platform, a ship, a floating production storage and offloading (FPSO) unit, etc.). The first separated fluid portion that is delivered through the production flow conduit 120 can include oil and/or gas, for example. The marine vessel 122 includes production equipment 123 that can extract the hydrocarbons from the production flow conduit 120 for storage in storage tanks on the marine vessel 122.

The second separated fluid portion passed through the injection flow conduit 124 to injection wellhead equipment 126. The second separated fluid includes primarily a target fluid (or target fluids), due to the fluid separation performed by the fluid separator 118. For example, the target fluid can include water. The second separated fluid portion is flowed through the injection flow conduit 124 and the injection wellhead equipment 126 for injection into the injection well 104. The injected fluid is stored in the reservoir 112.

Environmental regulations, standards, or criteria can specify that the second separated fluid portion to be injected into the injection well 104 for storage in the reservoir 112 should not include concentrations of certain types of particles that exceed specific thresholds. The particles can include fluid particles (e.g. oil droplets or other types of fluid particles) and/or solid particles (e.g. sand particles or other types of solid particles).

As an example, although the second separated fluid portion that is supplied by the fluid separator 118 into the injection flow conduit 124 includes primarily water, the second separated fluid portion can also include other particles, such as oil droplets and sand particles. If the concentrations of such other particles exceed specified thresholds, then violations of environmental regulations, standards, or criteria may occur. Also, excessive concentrations of certain particles may cause clogging of the injection well 104.

Based on the monitoring performed according to some implementations, actions can be taken in response to parameters associated with the monitored fluid not meeting thresholds.

In accordance with some implementations, a remote imaging-based measurement device 128 can be provided to measure the content of the second separated fluid portion in the injection flow conduit 124. The imaging-based measurement device 128 includes a light source (or multiple light sources) and an image sensor (or multiple image sensors).

Measurement data acquired by the imaging-based measurement device 128 can be used to determine one or more characteristics of the second separated fluid portion in the injection flow conduit 124. Such characteristics can include any or some combination of the following: a concentration of a particle (fluid particle and/or solid particle), a size of a particle, a type of a particle, a shape of a particle, a flow rate of the second separated fluid portion, and a velocity of a particle. The flow rate of a fluid portion can be derived from the velocity of a particle (or velocities of particles) in the fluid portion.

The imaging-based measurement device 128 is part of a fluid measurement system that is able to employ any of various particle measurement techniques. The particle measurement techniques can employ any or some combination of the following: high-speed imaging, multiple exposure imaging, and fluorescence imaging (discussed further below). The particle measurement system is able to determine quantities of particles (e.g. concentrations of particles, density of particles, composition of a fluid, flow rate of a fluid, velocities of particles, etc.). The particle measurement system can also provide information that can be displayed for viewing by users. Determining a velocity of a particle in the fluid portion in the injection fluid conduit 124 can include determining an instantaneous velocity of the particle within a specified time window.

In some implementations, the imaging-based measurement device 128 includes an imaging processor to perform analysis of measurement data collected by the image sensor(s) in the imaging-based measurement device 128, to determine one or more characteristics of the fluid portion in the injection flow conduit 124.

In further implementations, the imaging-based measurement device 128 can be deployed for a long time duration (e.g. up to about five years or more). The imaging-based measurement device 128 can be provided with the following characteristics: increased reliability, easy maintenance, ease of use in remote locations, easy connectivity, self-cleaning capabilities, and so forth.

In some implementations, the fluid measurement system can further include a surface controller 130, which can be provided on the marine vessel 122. The surface controller can include a computer or an arrangement of computers. Personnel on the marine vessel 122 can interact with the surface controller 130.

The surface controller 130 can also perform analysis to perform determination of one or more characteristics of the fluid portion in the injection flow conduit 124. In some examples, raw measurement data collected by the imaging-based measurement device 128 can be communicated to the surface controller 130 over a communication link 129 (e.g. electrical link, optical link, etc.). The surface controller 130 can apply processing of the raw measurement data to determine the one or more characteristics of the fluid portion in the injection flow conduit 124.

In further examples, the output produced by the imaging processor in the imaging-based measurement device 128 can be communicated to the surface controller 130 over the communication link 129. This output can include characteristics of the fluid portion in the injection flow conduit 124 as determined by the imaging processor of the imaging-based measurement device 128.

In accordance with some implementations, measurements made by the fluid measurement system (which can include the imaging-based measurement device 128 and the surface controller 130) can be performed in real time as fluid flows through the injection flow conduit 124. Performing the measurements in real time can refer to acquiring measurement data relating to the fluid portion in the injection flow conduit 124 as the fluid portion flows in the injection flow conduit 124. In further implementations, the determination of one or more characteristics of the fluid portion in the injection flow conduit 124 can also be performed in real time, as the measurement data is acquired by the imaging-based measurement device 128.

Although not shown, the arrangement shown in FIG. 1 can include other measurement devices, including sensors, test devices, and so forth, to monitor fluid flow in various parts of the production and/or injection arrangement.

Also, although reference is made to measuring content of a fluid portion in the injection flow conduit 124, it is noted that in other implementations, the fluid measurement system can be used to measure content of fluid flow in other flow conduits, such as the flow conduit 116, the product flow conduit 120, a tubing in the production well 102, a tubing in the injection well 104, and so forth.

Figure 2:
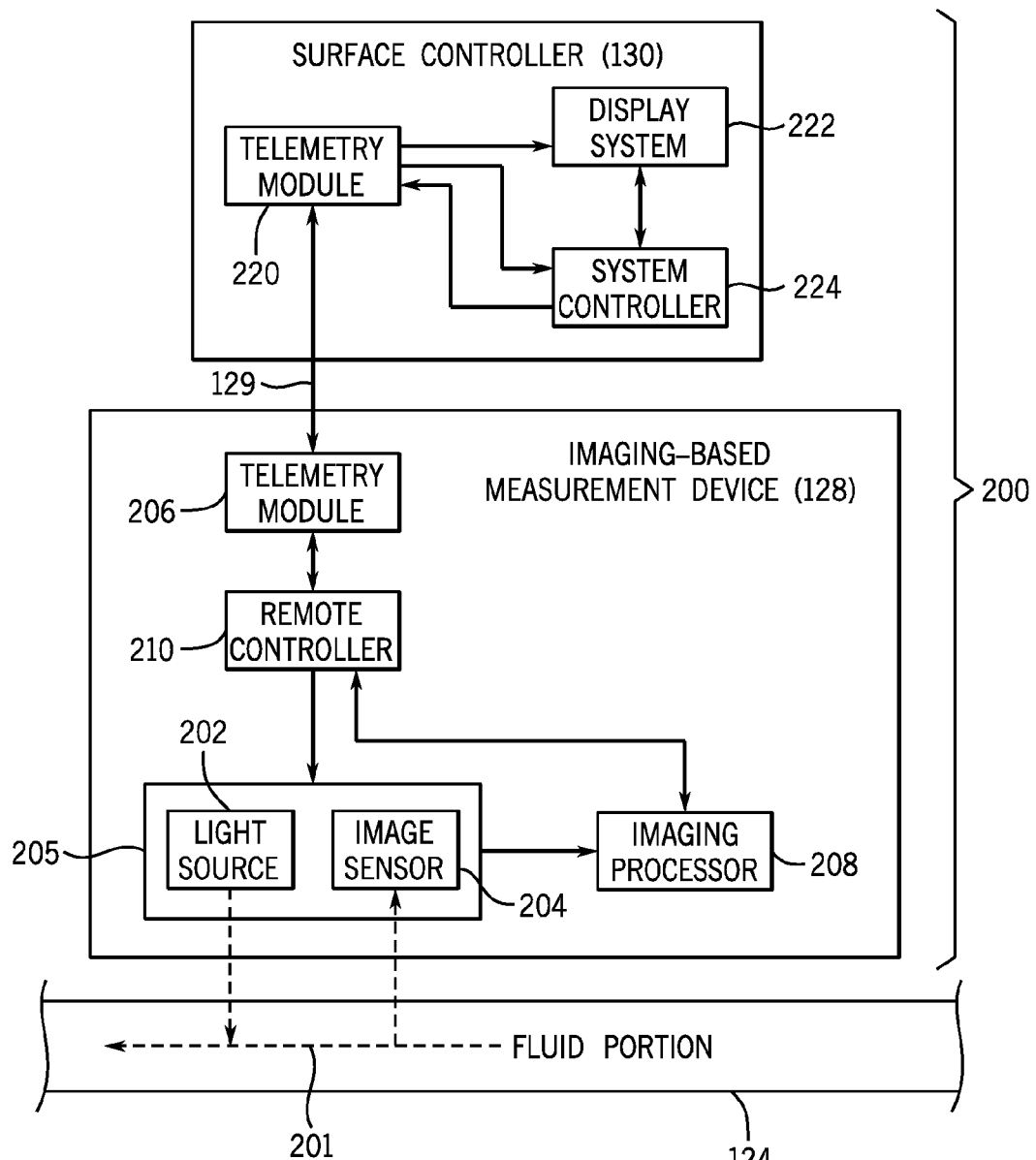
FIG. 2 is a block diagram of a fluid measurement system including a surface controller and a remote imaging-based measurement device, according to some implementations.

FIG. 2 shows an example of a fluid measurement system 200 that includes the remote imaging-based measurement device 128 and the surface controller 130. The remote imaging-based measurement device 128 is used to measure content of a fluid portion 201 that flows through the injection flow conduit 124 (or another flow conduit).

The remote imaging-based measurement device 128 includes a light source 202 and an image sensor 204. Note that although reference is made to a single light source 202 and a single image sensor 204, other implementations of the imaging-based measurement device 128 can employ multiple light sources and/or multiple image sensors. The light source(s) 202 and the image sensor(s) 204 are part of a remote monitoring fluid sensing unit 205. Multiple light sources and/or multiple image sensors can be used to acquire a three-dimensional (3D) image to allow for more accurate determination of characteristics of a fluid portion.

The light source 202 can include a laser source, a high intensity light source (such as a halogen lamp, etc.), or any other type of light source. The image sensor 204 can include a camera that is used to capture an image of fluid flowing through the flow conduit 124, or any other type of image sensor. As examples, the image sensor 204 can include a CMOS (complementary metal-oxide-semiconductor) image sensor, a CCD (charge-coupled device) camera, and so forth.

The remote monitoring fluid sensing unit 205 may be provided with a high speed capability for measuring high speed particle movement. High speed particle movement may be at speeds of, for example, up to about 3 meters per second (m/s). As examples, the camera 204 can be provided with a fast shutter speed, or the light source 202 can be provided with the ability to generate fast strobe light pulses. A shutter speed relates to a length of time that the shutter of the camera 204 is open when acquiring an image. A fast shutter speed refers to a speed of the camera shutter that is able to image high speed movement of particles in the fluid portion 201, without blurring. For example, the camera may be able to take millions of frames per second. In other examples, the camera may be able to take hundreds or thousands of frames per second.

The light source 202 is able to produce a sequence of light pulses, where the time interval between the light pulses can be short enough to adequately image high speed movement of particles in the fluid portion 201. An example of the light source 202 that can provide fast strobe light pulses can include a high frequency pulsed laser source using Particle Image Velocimetry (PIV). For example, the light pulses can be generated at a frequency greater than about 10 megahertz (MHz). PIV may be used to perform quantitative measurement of fluid velocity at multiple points. PIV may employ a double-exposure (or multiple exposure) technique using a high frequency pulsed laser source and/or a multiple wavelength laser source pulsed with a single camera exposure. Various algorithms can be used to measure velocity of each particle in a flow of the fluid portion 201.

The imaging-based measurement device 128 includes a telemetry module 206, which is able to communicate data over the communication link 129 with the surface controller 130.

Raw measurement data acquired by the remote monitoring fluid sensing unit 205 (more specifically, the image sensor 204) can be provided to an imaging processor 208. The imaging processor 208 can process the raw measurement data from the remote monitoring fluid sensing unit 205 to determine one or more characteristics of the fluid portion 201, as discussed above. In some examples, the raw measurement data can also be sent by the telemetry module 206 over the communication link 129 to the surface controller 130.

The remote monitoring fluid sensing unit 205 is operatively coupled to the fluid portion 201 flowing in the flow conduit 124. For example, the remote monitoring fluid sensing unit 205 can either be in contact with or located at least partially inside the flow conduit 124.

The imaging processor 208 can perform real-time measurements. In some examples, the imaging processor 208 can use high-speed vision pixel massively parallel processing to process measurement data from the remote monitoring fluid sensing unit 205 to determine the characteristics of the fluid portion 201. Examples of image processing that can be performed by the imaging processor 208 include image processing described in any of the following: U.S. Publication No. 2013/0265409; Yoshihiro Watanabe et al., "Real-Time Visual Measurements Using High-Speed Vision," Proceedings of SPIE Vol. 5603, 2004. In other examples, other image processing techniques can be applied, such as 3D imaging and tomography.

In some examples, the imaging processor 208 is located in situ with the remote monitoring fluid sensing unit 205. For example, the imaging processor 208 can be part of the same module (located within a housing of the module) as the remote monitoring fluid sensing unit 205. As another example, the imaging processor 208 can be mounted on a common circuit board as the remote monitoring fluid sensing unit 205.

The imaging-based measurement device 128 can also include a remote controller 210, which can control the remote monitoring fluid sensing unit 205 and the imaging processor 208. Also, as shown in FIG. 2, communications through the telemetry module 206 also pass through the remote controller 210. In other examples, the remote controller 210 is not in the data path with the telemetry module 206.

The remote controller 210 can control when the remote monitoring fluid sensing unit 205 and/or the imaging processor 208 are activated. Moreover, the remote controller 210 can communicate over the communication link 129 with the surface controller 130. The surface controller 130 can send commands to the remote controller 210 to control acquisition of measurement data and processing of the measurement data.

The surface controller 130 includes a telemetry module 220 to allow the surface controller 130 to communicate over the communication link 129 with the remote imaging-based measurement device 128. In addition, the surface controller 130 includes a display system 222. Data received by the telemetry module 220 from the remote imaging-based measurement device 128 can be passed for display by the display system 222. The displayed data can include various characteristics determined by the imaging processor 208.

In response to the displayed data, a user (e.g. operator) can take appropriate action. For example, the user can issue a command to a system controller 224 in the surface controller 130. In response, the system controller 224 can send a correspond command to the remote imaging-based measurement device 128 or to another remote module to cause an action to be performed.

Data received by the telemetry module 220 from the remote imaging-based measurement device 128 can also be passed to the system controller 224. The received data can include information pertaining to characteristics of the fluid portion 201 as determined by the imaging processor 208, or the received data can include raw measurement data from the remote monitoring fluid sensing unit 205. Based on the received data, the system controller 224 can determine whether an alarm or other notification should be generated to a user (the alarm or other notification can be displayed by the display system 222. As further examples, based on the received data, the system controller 224 can determine whether another action should be taken. For example, the system controller 224 can automatically generate a command to the imaging-based measurement device 128 or another module, such as if an emergency or other urgent condition is indicated by the received data.

If the received data is raw measurement data, the system controller 224 can also perform analysis to determine one or more of characteristics of the fluid portion 201 in the flow conduit 124.

Figure 3A:
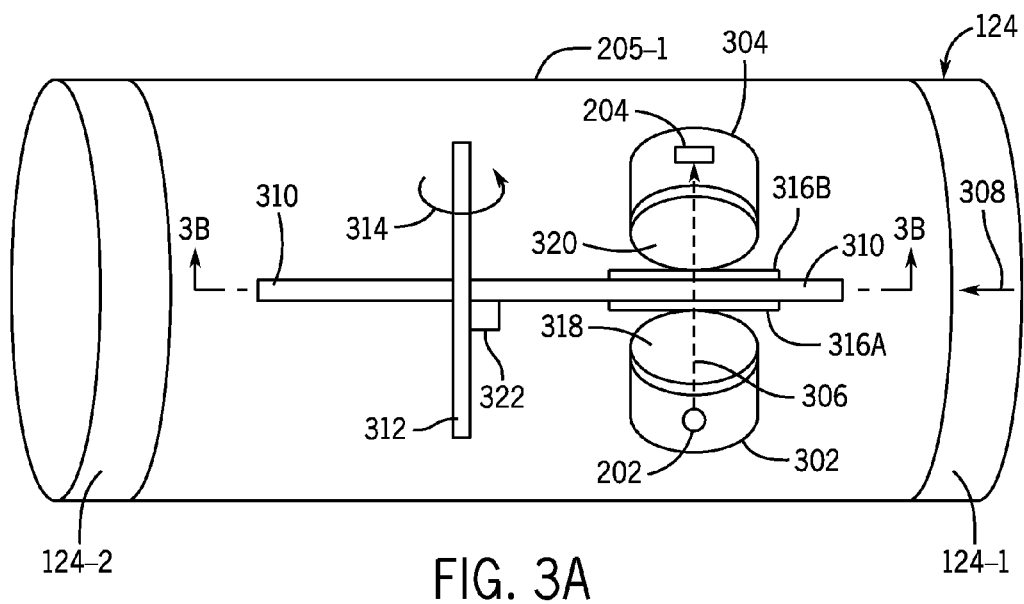
FIG. 3A is a schematic diagram of a fluid sensing unit including a cleaner in accordance with some implementations.

FIG. 3A illustrates an example of a fluid sensing unit 205-1 (which is an example of the fluid sensing unit 205 of FIG. 2) according to some implementations. The fluid sensing unit 205-1 can be in the form of a module or insert that can be provided between segments 124-1 and 124-2 of the flow conduit 124. The fluid sensing unit 205-1 can have a tubular housing in which are provided various components as depicted in FIG. 3A. The tubular housing can have a circular cross-sectional shape, or another shape. Fluid 308 flowing in the fluid flow segment 124-1 can flow into the fluid sensing unit 205-1, and can then exit from the fluid sensing unit 205-1 to the fluid conduit segment 124-2. The components of the fluid sensing unit 205-1 can be considered to be positioned inside an overall flow conduit that includes the segments 124-1 and 124-2 and the flow path inside the fluid sensing unit 205-1.

The fluid sensing unit 205-1 includes a light source unit 302 and an image sensor unit 304. The light source unit 302 includes the light source 202, which can emit light along a light path represented by arrow 306 towards the image sensor unit 304. The image sensor unit 304 includes the image sensor 204

The light source unit 302 and the image sensor unit 304 are spaced apart from each other, such that a portion of a fluid 308 that flows through the flow conduit 124 can pass between the units 302 and 304.

In addition, in the space between the units 302 and 304, a rotatable structure 310 is provided that is rotatable about a support axle 312 that defines a rotation axis. The support axle 312 is supported by the housing of the fluid sensing unit 205-1. The support axle 312 is generally perpendicular to the longitudinal axis of the flow conduit 124, where the longitudinal axis is parallel to the direction of the flow of the fluid 308. Rotation of the rotatable structure 310 is represented by arrow 314.

Figure 3B:
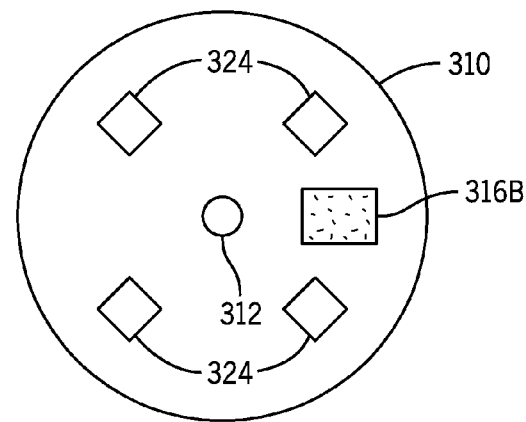
FIG. 3B is a top view of a rotatable structure in the fluid sensing unit of FIG. 3A according to some examples.

The rotatable structure 310 can be a disk that has a generally circular shape, as shown in FIG. 3B. In other examples, the rotatable structure 310 can have different shapes. Mounted on the rotatable structure 310 are cleaning elements 316A and 316B for cleaning respective optical windows 318 and 320. The optical window 318 is attached to a housing of the light source unit 302, and the optical window 320 is attached to a housing of the image sensor unit 304. Each optical window 318 or 320 can be formed of sapphire or some other transparent material through which the light emitted by the light source 202 can pass.

The optical windows 318 and 320 can be sealingly attached to the respective housings of the units 302 and 304. The sealing attachment can be performed using an elastomer seal, a metalized brazing seal, or a metal-to-metal seal, as examples.

A blade or rudder 322 is arranged on the rotatable structure 310 and/or the support axle 312. The blade 322 is driven by the force of the fluid 308 flowing through the flow conduit 124. As the fluid 308 flows in the flow conduit 124, the fluid flow applies a force on the blade 322, which causes rotation of the rotatable structure 310. Rotation of the rotatable structure 310 allows the cleaning elements 316A and 316B to brush against the optical windows 318 and 320, respectively, to clean debris off the optical windows.

The cleaning elements 316A and 316B can be coated with a cleaning material, such as a microfiber, a cleaning pad, or some other type of material. Note that the cleaning material can be coated to a respective surface of the rotatable structure 310.

FIG. 3B shows a top view of the rotatable structure 310. The rotatable structure 310 is rotatable about the support axle 312. Windows 324 are formed in the rotatable structure 310. The windows 324 can include voids in the rotatable structure 310, or optical windows such as sapphire or another transparent material. Although four windows 324 are shown in FIG. 3B, it is noted that in other examples, a different number of windows 324 can be provided (e.g. one or greater than one).

FIG. 3B also shows the cleaning element 316B provided on the upper surface of the rotatable structure 310. Although just one cleaning element 316B is shown, it is noted in other examples, more than one cleaning element 316B can be provided on the rotatable structure 310. The cleaning element 316A provided on the lower surface of the rotatable structure 310 is not shown in FIG. 3B.

When a window 324 is aligned with the light source unit 302 and the image sensor unit 304, the light emitted by the light source 202 can pass through the aligned window 324 to the image sensor unit 304. Note that when a window 324 is not aligned with the units 302 and 304, then light emitted by the light source 202 would be blocked by the rotatable structure 310, and thus would not be able to pass to the image sensor unit 304.

In the arrangement of FIG. 3A, the windows 324 in the rotatable structure 310, and the optical windows 318 and 320, can be considered examples of optical elements that are positioned inside a flow conduit. An optical element is positioned inside a flow conduit if the optical element is within an inner chamber of the flow conduit.

Figure 3C:
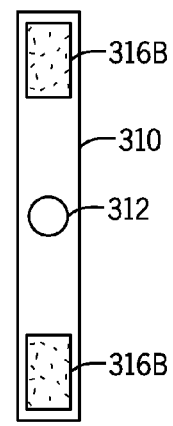
FIG. 3C is a top view of a rotatable structure in the fluid sensing unit of FIG. 3A according to further examples.

In other examples, multiple fins of the rotatable structure 310 can be provided with cleaning elements 316B, as shown in FIG. 3C. In the latter examples, the rotatable structure 310 is not disk-shaped, but rather has an elongated shape. Light can pass on either side of the elongated rotatable structure 310.

Figure 4:
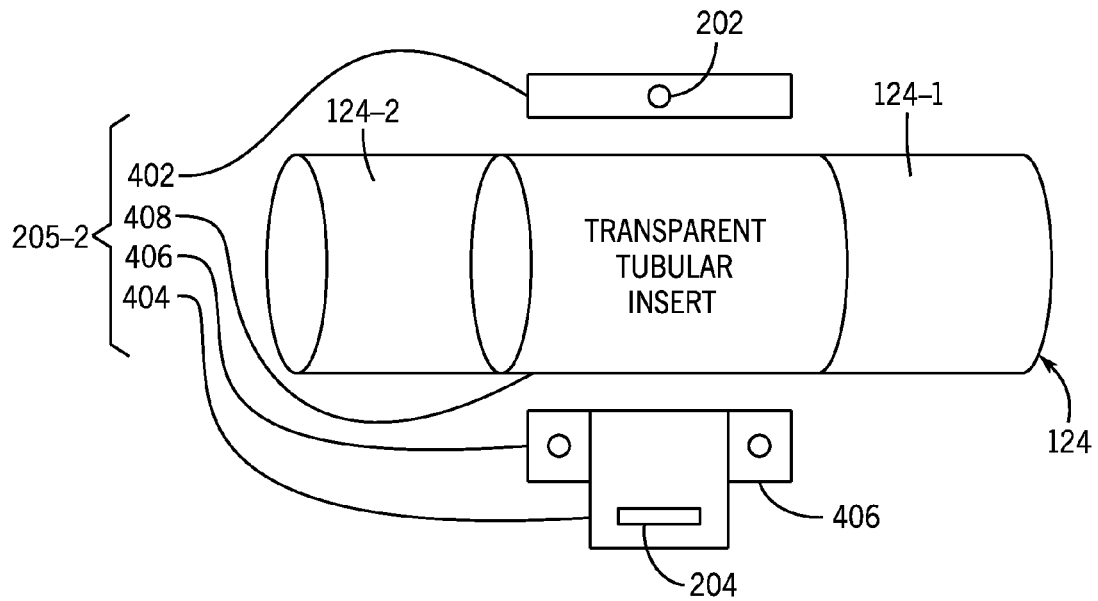
FIG. 4 is a schematic diagram of a fluid sensing unit including a transparent tubular insert in accordance with some implementations.

FIG. 4 is a schematic diagram of a fluid sensing unit 205-2 according to further examples. The fluid sensing unit 205-2 includes a light source unit 402 that includes the light source 202, and an image sensor unit 404 that includes the image sensor 204. The light source unit 402 and the image sensor unit 404 are positioned on opposite sides of the flow conduit 124 of FIG. 4.

In some examples, the fluid sensing unit 205-2 can include a light source unit or multiple light source units 406 positioned on the same side as the image sensor unit 404, either in addition to or in place of the light source unit 402.

The fluid sensing unit 205-2 further includes a transparent tubular insert 408 that is attached between non-transparent tubular segments 124-1 and 124-2 of the flow conduit 124. The transparent tubular insert 408 can have a circular cross-sectional shape, or another shape.

The transparent tubular insert 408 can have a transparent wall, which can be made of sapphire or other transparent material. The transparent wall of the transparent tubular insert 408 allows light to pass from a light source unit (e.g. 402 or 406) into the inner chamber of the flow conduit 124. Light affected or reflected by a portion of the fluid inside the flow conduit 124 is received by the image sensor 204 in the image sensor unit 404.

Light emitted by the light source unit 402 propagates through the transparent wall of the transparent tubular insert 408 and passes to the image sensor unit 404. In other examples, light emitted by a light source unit 406 is propagated through the transparent wall of the transparent tubular insert 408, and is reflected by the portion of fluid in the flow conduit 124 back towards the image sensor unit 404.

Use of the transparent tubular insert 408 allows the light source unit(s) and image sensor unit to be positioned outside of the flow conduit 124, while still allowing for the image sensor unit 404 to measure the content of the fluid portion inside the flow conduit 124.

Figure 5:
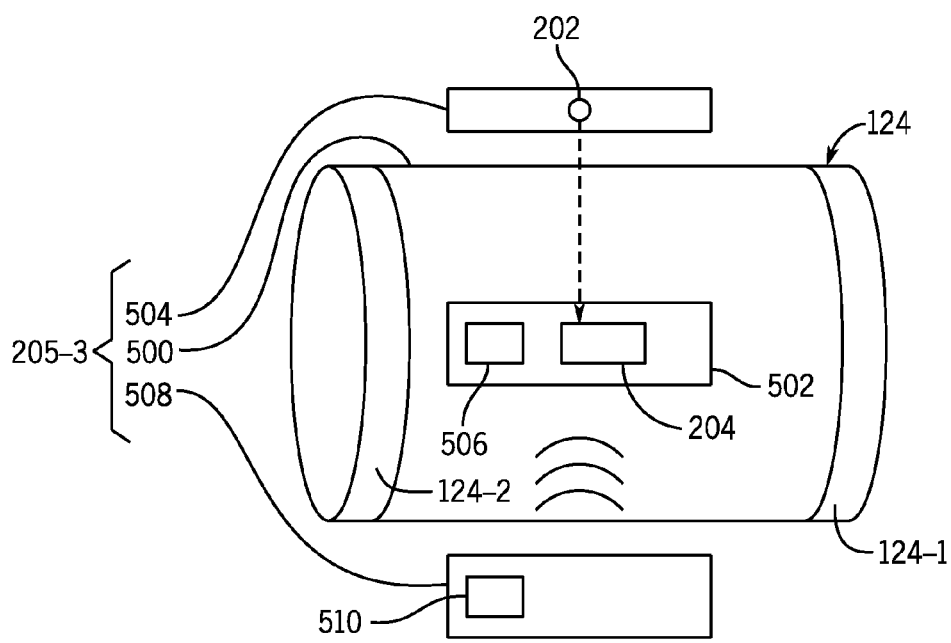
FIG. 5 is a schematic diagram of a fluid sensing unit including an internal image sensor unit and an external monitor unit in accordance with some implementations.

FIG. 5 illustrates a fluid sensing unit 205-3 according to additional examples. The fluid sensing unit 205-3 includes an image sensor module or insert 500. The image sensor module 500 is connected between fluid conduit segments 124-1 and 124-2. The image sensor module 500 includes an image sensor unit 502 positioned inside an inner chamber of the image sensor module 500. The image sensor unit 502 includes the image sensor 204. The fluid sensing unit 205-3 also includes a light source unit 504 and a monitor unit 508. Fluid flowing in the flow conduit segment 124-1 can flow into the image sensor module 500, and then out into the flow conduit segment 124-2.

Light emitted by the light source 202 in the light source unit 504 can be propagated into the inner chamber of the flow conduit 124, either through a transparent optical window or through the transparent wall of a transparent tubular insert (similar to that depicted in FIG. 4).

Measurement data acquired by the image sensor 204 can be communicated to a wireless telemetry module 506 that is part of the image sensor unit 502. The wireless telemetry module 506 can perform wireless communications with the monitor unit 508 that is located outside the flow conduit 124. The wireless communication can include electromagnetic (e.g. radio frequency) communication. The monitor unit 508 includes a wireless telemetry module 510 to communicate with the wireless telemetry module 506.

In some examples, the image sensor unit 502 inside the flow conduit 124 can be powered using electromagnetic power from the monitor unit 508. In other examples, the image sensor unit 502 can include a battery. In other examples, other mechanisms for powering the image sensor unit 502 can be employed.

To allow for electromagnetic communication between the wireless telemetry modules 506 and 510, a portion of the housing of the flow conduit 124 can be formed using a composite material instead of a metal or magnetic material.

The monitor unit 508 can include a storage device to store the measurement data, and can also include a communication element to communicate the measurement data received by the wireless telemetry module 510 to another element, such as the imaging processor 208 (FIG. 2).

Figure 6A:
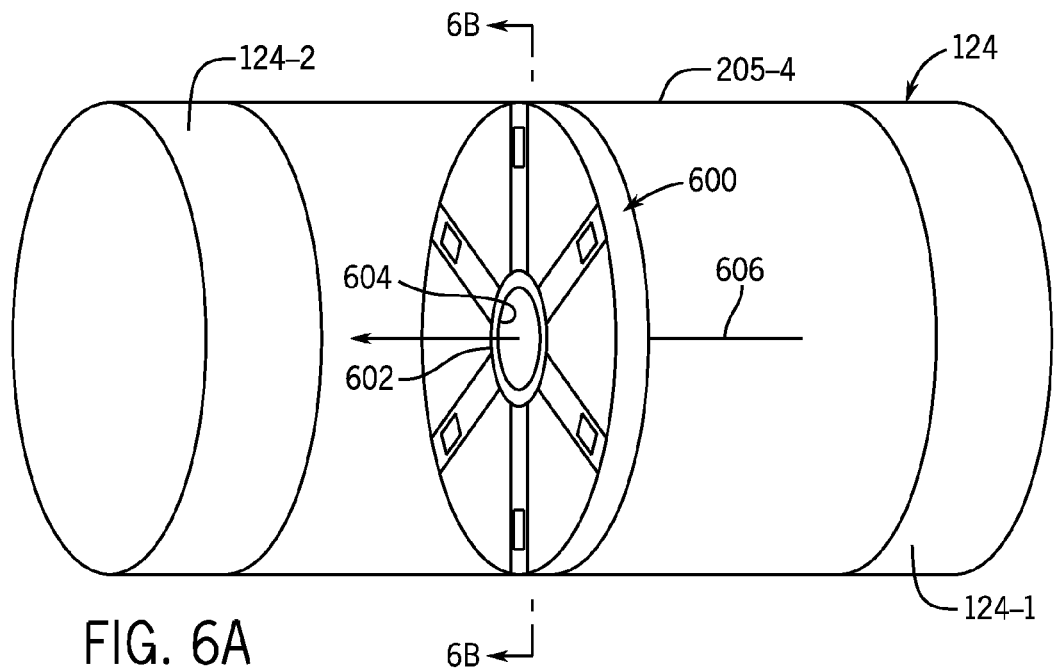
FIG. 6A is a schematic diagram of a fluid sensing unit including a measurement hub with radial optical structures in accordance with some implementations.
Figure 6B:
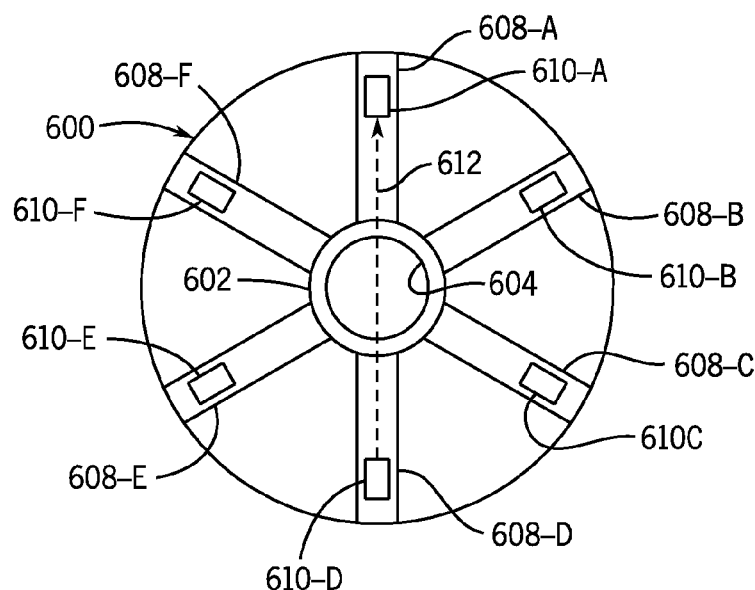
FIG. 6B is a cross-section view of the fluid sensing unit of FIG. 6A.

FIGS. 6A and 6B illustrate a fluid sensing unit 205-4 according to further implementations. The fluid sensing unit 205-4 can be in the form of a module or insert connected between the fluid conduit segments 124-1 and 124-2. FIG. 6B is a cross-sectional view of a structure 600 of the fluid sensing unit 205-4 that is positioned inside the inner chamber of the fluid sensing unit 205-4 of FIG. 6A. The structure 600 includes a central hub 602 that includes an opening 604 through which fluid 606 flowing in the flow conduit 124 can pass. Radial optical structures 608-A to 608-F are attached to the central hub 602 and extend radially outwardly from the hub 602. Each radial optical structure 608 (any of 608-A to 608-F) can include an optical fiber rod or an optical lens or any other structure that allows for light to propagate through the optical structure 608.

An active optical element 610 (any of optical elements 610-A to 610-F) can be provided in the respective radial optical structure 608. An active optical element can include a light source and/or an image sensor. For example, the active optical element 610-A can include an image sensor, while the active optical element 610-D can include a light source. The light source 610-D can emit light that passes through the opening 604 of the hub 602 and to the image sensor 610-A, as indicated by arrow 612. The light that passes along the light path 612 is affected by a portion of the fluid 606 flowing in the fluid sensing unit 205-4 (received from the flow conduit 124). In this way, the image sensor 610-A can measure the content of the portion of the fluid 606 that passes through the opening 604.

Other combinations of light sources and image sensors can be provided in the radial optical structures that are part of the fluid sensing unit 205-4.

A fluid measurement in which light from the light source 610-D passes through the opening 604 to the image sensor 610-A is an example of a transmittance-based measurement.

In other examples, reflection-based measurement can also be performed, where light from a light source can be reflected from the fluid portion in the opening 604 towards an image sensor that is provided in one of the radial optical structures 610-A to 610-F.

In further examples, a combination of light sources and image sensors can provide 3D imaging which can prevent an overlap image of a fluid particle. Also, utilizing radial optical structures, 3D measurement (tomography) can be realized.

Figure 7:
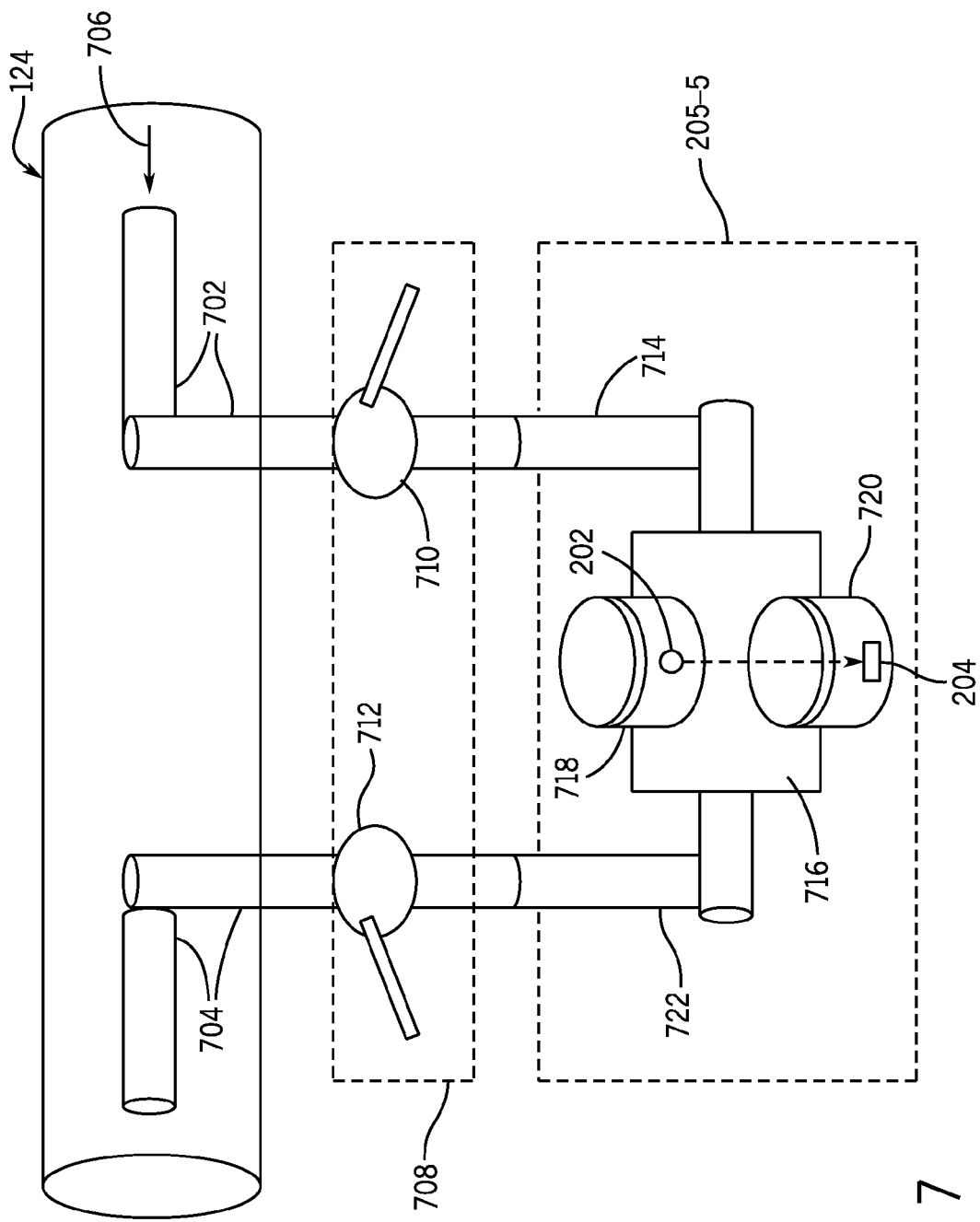
FIG. 7 is a schematic diagram of a fluid sensing unit including a flow circuit in accordance with some implementations.

FIG. 7 is a schematic diagram illustrating a fluid sensing unit 205-5 that can be positioned outside of the flow conduit 124. However, to allow for measurement of the content of a portion of fluid 706 in the flow conduit 124, a flow circuit is provided to communicate the portion of the fluid 706 to the fluid sensing unit 205-5. The flow circuit includes flowlines 702 and 704 that can be connected to communicate with the flow conduit 124. The portion of the fluid 706 in the flow conduit 124 can flow into the flowline 702. A flow control mechanism 708 connected to the flowlines 702 and 704 can be actuated between an open position and a closed position. The flow control mechanism 708 can include valves 710 and 712 connected to the respective flowlines 702 and 704.

If the valves in 710 and 712 are open, then the fluid portion flowing into the flowline 702 is able to pass from the flowline 702 through a flowline 714 into a measurement chamber 716 of the fluid sensing unit 205-5. A light source unit 718 is provided on one side of the measurement chamber 716, and an image sensor unit 720 is provided on the opposite side of the measurement chamber 716. In other words, the units 718 and 720 are spaced apart by at least a portion of the measurement chamber 716. Light from the light source 202 in the light source unit 718 is emitted towards the image sensor unit 720.

Fluid flowing through the measurement chamber 716 can continue through a flowline 722 through the open valve 712 and back to the flowline 704. The fluid can then exit the flowline 704 back into the flow conduit 124.

When the valves 710 and 712 are actuated to the closed position, fluid does not flow through the flowlines 702, 714, 722, and 704.

Actuation of the flow control mechanism 708 (including the valves 710 and 712) between the open position and closed position can be accomplished in one of several manners. For example, a remote operating vehicle (ROV) in a marine environment can be used to actuate the valves 710 and 712. In other examples, a control line connected to a remote location, such as a marine vessel or other entity, can be used to actuate the flow control mechanism 708.

Note that the fluid sensing unit 205-5 can be removably connected to the flow control mechanism 708. The fluid connections between the fluid sensing unit 205-5 and the flow control mechanism 708 can be a quick connect mechanism to allow for quick connection and disconnection, in some examples.

Figure 8:
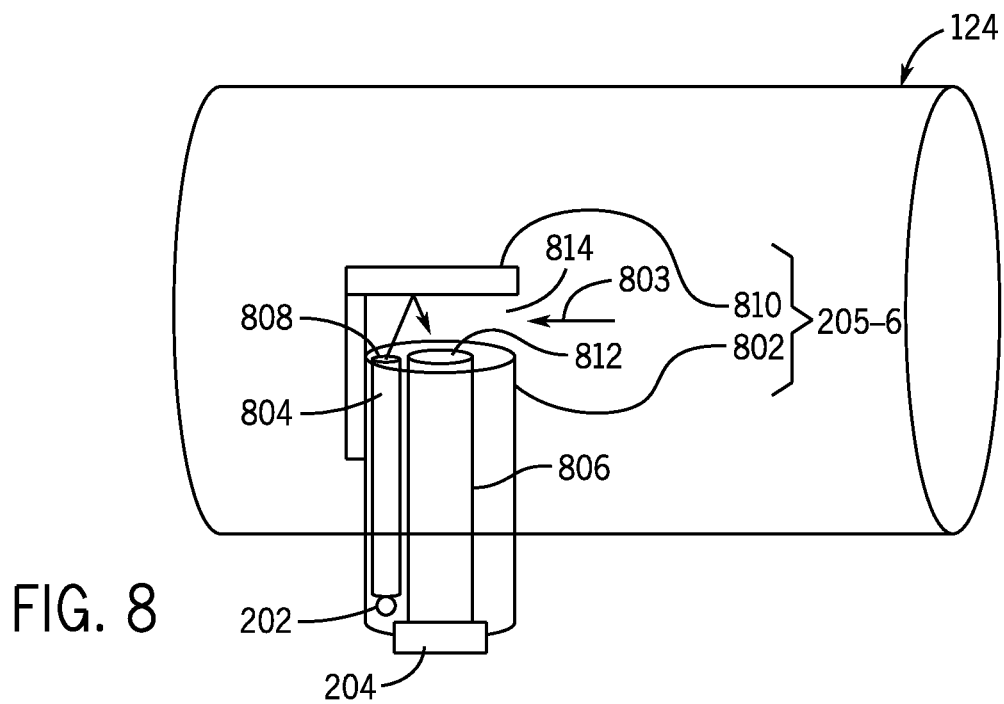
FIG. 8 is a schematic diagram of a fluid sensing unit including optical fibers and an optical reflector in accordance with some implementations.

FIG. 8 shows a fluid sensing unit 205-6 according to further implementations. The fluid sensing unit 205-6 includes a structure 802 that includes a first optical fiber 804 that is optically coupled to the light source 202, and a second optical fiber 806 that is coupled to the image sensor 204. The first optical fiber 804 can be referred to as a lighting fiber, while the second optical fiber 806 can be referred to as a viewing fiber. The optical fibers 804 and 806 can be in the form of optical fiber rods or bundles.

Light emitted by the light source 202 passes through the lighting fiber 804 and out from an end 808 of the lighting fiber 804. The light emitted from the end of the lighting fiber 804 propagates towards an optical reflector 810 (e.g. a mirror), and the light is reflected back to an end portion 812 of the viewing fiber 806. The reflected light propagates through the viewing fiber 806 to the image sensor 204.

A gap 814 is provided between the top portion of the structure 802 and the optical reflector 810, such that fluid 803 flowing in the flow conduit 124 can pass through the gap 814.

Figure 9:
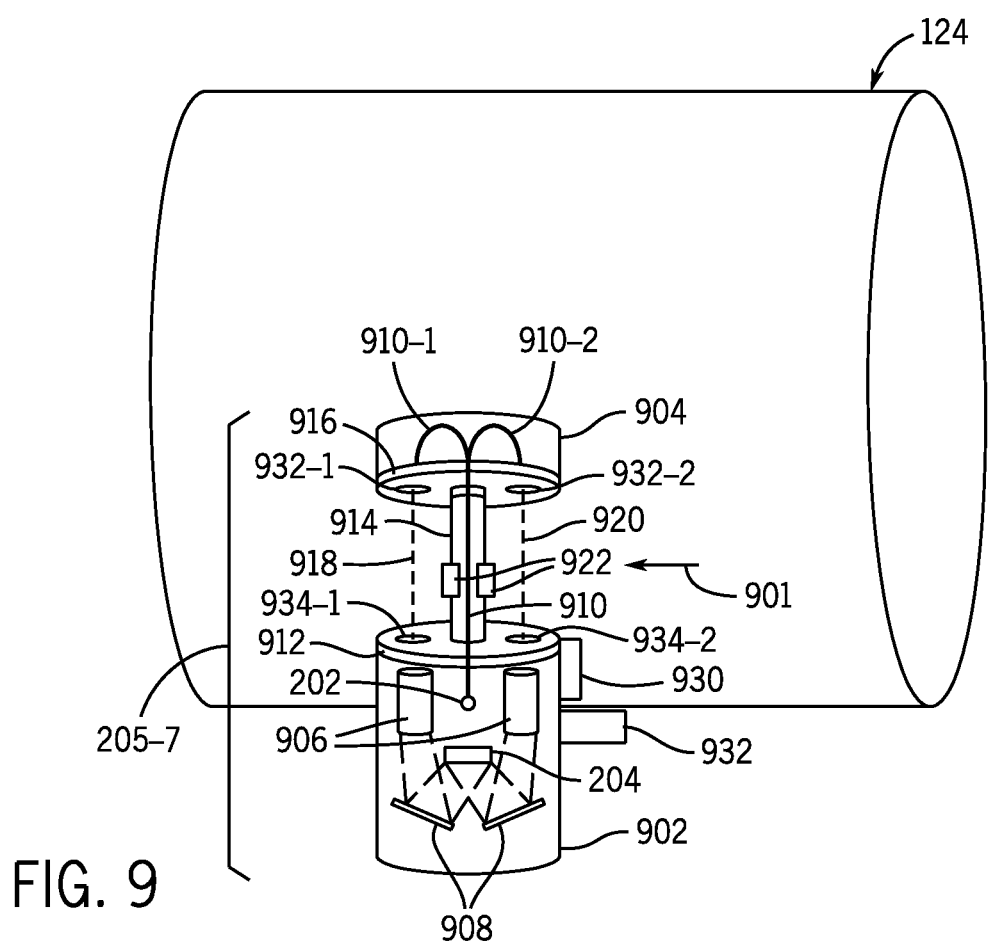
FIG. 9 is a schematic diagram of a fluid sensing unit including non-rotatable housing structures, rotatable structures, and optical fibers in accordance with some implementations.

FIG. 9 is a schematic diagram of a fluid sensing unit 205-7 according to other implementations. The fluid sensing unit 205-7 includes a first non-rotatable housing structure 902 and a second non-rotatable housing structure 904. The non-rotatable housing structure 902 contains the image sensor 204 and the light source 202. In addition, lenses 906 and optical reflectors 908 are provided to direct light towards the image sensor 204.

Optical fibers 910 are optically coupled to the light source 202. Light generated by the light source 202 is propagated the optical fibers 910, which are lighting fibers. The optical fibers 910 pass through a hole (or holes) in a rotatable structure 912 that is mounted to and rotatable with respect to the non-rotatable housing structure 902. The optical fibers 910 further pass through an inner channel of a rotatable rod 914 and through a hole (or holes) of a rotatable structure 916 that is mounted to and rotatable with respect to the non-rotatable housing structure 904.

The rod 914 and rotatable structures 912 and 916 are attached together, such that the rod 914 and the rotatable structures 912 and 916 rotate together. The rod 914 is attached to one or more blades or rudders 922. Fluid flowing in the flow conduit 124 applies a force on the blades 922 to cause rotation of the rod 914, and thus, corresponding rotation of the rotatable structures 912 and 916.

The optical fibers 910 extend into an inner chamber of the non-rotatable housing structure 904. The optical fibers 910 inside the non-rotatable housing structure 904 are split into an optical fiber 910-1 and an optical fiber 910-2 that are then arranged to direct light to respective optical windows of the non-rotatable housing structure 904 (discussed in connection with FIG. 10). The light running through the optical fibers 910-1 and 910-2 can be emitted through the optical windows of the non-rotatable housing structure 904, for propagation along respective optical paths 918 and 920 towards the rotatable structure 912 and the non-rotatable housing structure 902.

Figure 10:
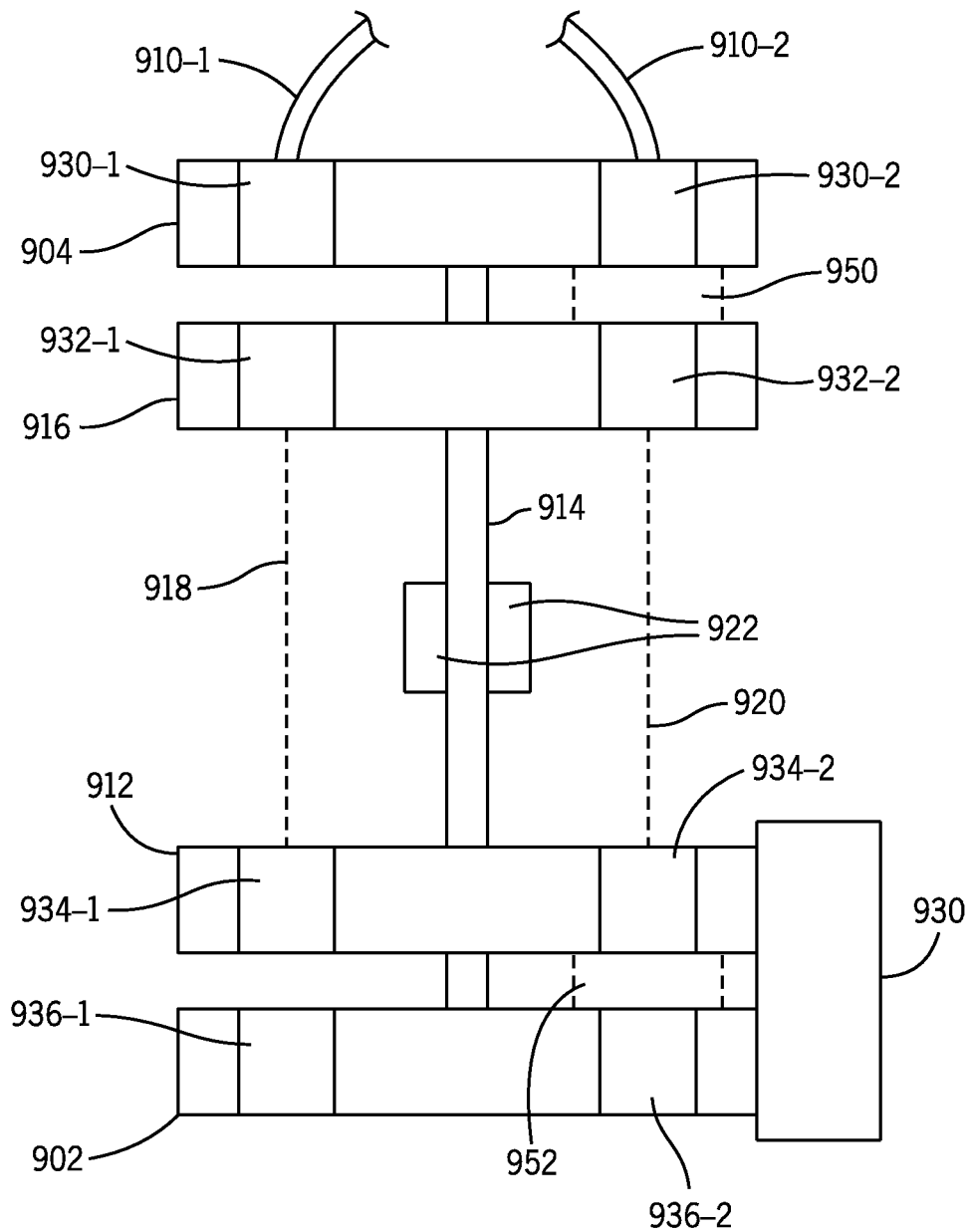
FIG. 10 is a schematic diagram illustrating a portion of the fluid sensing unit of FIG. 9.

As further shown in FIG. 10, the non-rotatable housing structure 904 has optical windows 930-1 and 930-2 (formed of sapphire or other transparent material). Ends of the optical fibers 910-1 and 910-2 are positioned adjacent the optical windows 930-1 and 930-2, such that light propagated through the optical fibers 910-1 and 910-2 can be emitted through the optical windows 930-1 and 930-2.

The rotatable structure 916 has windows 932-1 and 932-2 (voids or optical windows) that when aligned with the optical windows 930-1 and 930-2 of the non-rotatable housing structure 904 allow light to propagate through the windows 932-1 and 932-2 to the respective optical paths 918 and 920.

The rotatable structure 912 similarly includes windows 934-1 and 934-2 (voids or optical windows). The non-rotatable housing structure 902 also similarly includes optical windows 936-1 and 936-2. When the windows 934-1 and 934-2 are aligned with respective windows 936-1 and 936-2, light along the optical paths 918 and 920 can propagate through these respective windows to the corresponding lenses 906 in the non-rotatable housing structure 902.

As further shown in FIG. 9, a brake 930 is provided that can be controllably actuated to stop rotation of the rod 914 and the rotatable structures 912 and 916. When actuated, the brake 930 engages the rotatable structure 912 to prevent rotation of the rod 914 and the rotatable structures 912 and 916. When not actuated, the brake 930 disengages from the rotatable structure 912 and allows rotation of the rod 914 and the rotatable structures 912 and 916.

Actuation of the brake 930 may be controlled by a controller 932. The controller 932 can be, for example, a magnetic switch or electromagnetic switch positioned outside the flow conduit 124. Braking may be controlled from outside the flow conduit 124 using, for example, magnetic or electromagnetic (wireless) coupling.

In some examples, as further shown in FIG. 10, a cleaning element 950 can be provided on the rotatable structure 916 to clean the optical windows 930-1 and 930-2, and a cleaning element 952 can be provided on the rotatable structure 912 to clean the optical windows 936-1 and 936-2. The cleaning elements 950 and 952 are located on the rotatable structures 916 and 912, respectively.

The multiple optical paths 918 and 920 provide redundancy, where one optical path can be used if another optical path fails. In some examples, one or more of the optical paths may remain normally closed, in non-contact with fluid (e.g. protected by windows cap), and/or selectively opened when desired. Certain optical paths can remain closed to prevent dirt or debris from forming on optical windows, and may be used when transmission of light through another optical window is not possible, such as due to dirt or failure, for example.

In some implementations, the various fluid sensing units discussed herein can be deployed using an ROV or other vehicle.

In the foregoing description, numerous details are set forth to provide an understanding of the subject disclosed herein. However, implementations may be practiced without some of these details. Other implementations may include modifications and variations from the details discussed above. It is intended that the appended claims cover such modifications and variations.

What is claimed is:

1. An imaging-based measurement apparatus, comprising:
   a light source;
   at least one optical element for positioning in a flow conduit, the at least one optical element being part of a light path for light emitted by the light source, wherein light along the light path passes through a portion of fluid flowing in the flow conduit;
   an image sensor to detect the light and to measure content of the portion of the fluid; and
   a rotatable structure,
   wherein the at least one optical element comprises a window in the rotatable structure, the rotatable structure to rotate such that the light is able to pass through the window when the window is aligned with respect to the light source and the image sensor, and
   wherein at least one of the light source and the image sensor is part of a unit comprising an optical window through which the light is able to pass, and wherein the rotatable structure comprises a cleaning element to clean the optical window as the rotatable structure rotates.

2. The imaging-based measurement apparatus of claim 1, wherein the window comprises a void or a transparent material.

3. The imaging-based measurement apparatus of claim 1, further comprising a rotatable rod attached to the rotatable structure, and an optical fiber extending through an inner channel of the rotatable rod and through the rotatable structure to communicate the light emitted by the light source.

4. The imaging-based measurement apparatus of claim 3, further comprising a first non-rotatable housing structure, wherein the optical fiber extends into the first non-rotatable housing structure, the optical fiber to transmit the light through an optical window of the first non-rotatable housing structure.

5. The imaging-based measurement apparatus of claim 4, further comprising a second non-rotatable housing structure that comprises the image sensor, the rotatable rod separating the first and second non-rotatable housing structures, and the second non-rotatable housing structure comprising an optical window to receive the light passed through the optical window of the first non-rotatable housing structure and through the portion of the fluid.

6. The imaging-based measurement apparatus of claim 1, further comprising a brake that upon actuation stops rotation of the rotatable structure.

7. The imaging-based measurement apparatus of claim 1, wherein the flow conduit comprises a tubular conduit that has a transparent tubular insert, wherein the light is to pass through a transparent wall of the transparent tubular insert between the light source and the image sensor.

8. The imaging-based measurement apparatus of claim 1, wherein the image sensor is for positioning in the flow conduit and comprises a wireless telemetry module to communicate measured data with a monitor unit that is external of the flow conduit.

9. The imaging-based measurement apparatus of claim 1, wherein the at least one optical element comprises a hub and a plurality of radial optical structures extending from the hub.

10. The imaging-based measurement apparatus of claim 9, wherein the hub comprises an opening through which the portion of fluid flows, and wherein the light source and the image sensor are mounted in respective radial optical structures of the plurality of radial optical structures.

11. The imaging-based measurement apparatus of claim 10, wherein the plurality of radial optical structures comprise optical fiber rods or optical lenses.

12. The imaging-based measurement apparatus of claim 1, wherein the at least one optical element comprises an optical reflector.

13. The imaging-based measurement apparatus of claim 12, further comprising a first optical fiber to transmit the light towards the optical reflector, and a second optical fiber to receive reflected light from the optical reflector, wherein the portion of the fluid is to pass in a space between the first and second optical fibers and the optical reflector, and wherein the image sensor is optically coupled to the second optical fiber.

14. An imaging-based measurement method, comprising:
   emitting a light source;
   positioning at least one optical element in a flow conduit, the at least one optical element being part of a light path for light emitted by the light source, wherein light along the light path passes through a portion of fluid flowing in the flow conduit;
   using an image sensor to detect the light and to measure content of the portion of the fluid; and
   providing a rotatable structure,
   wherein the at least one optical element comprises a window in the rotatable structure, the rotatable structure to rotate such that the light is able to pass through the window when the window is aligned with respect to the light source and the image sensor, and
   wherein at least one of the light source and the image sensor is part of a unit comprising an optical window through which the light is able to pass, and wherein the rotatable structure comprises a cleaning element to clean the optical window as the rotatable structure rotates.

15. An imaging-based measurement apparatus, comprising:
   a light source;
   at least one optical element for positioning in a flow conduit, the at least one optical element being part of a light path for light emitted by the light source, wherein light along the light path passes through a portion of fluid flowing in the flow conduit;
   an image sensor to detect the light and to measure content of the portion of the fluid;
   a rotatable structure;
   a rotatable rod attached to the rotatable structure;
   an optical fiber extending through an inner channel of the rotatable rod and through the rotatable structure to communicate the light emitted by the light source; and
   a first non-rotatable housing structure,
   wherein the at least one optical element comprises a window in the rotatable structure, the rotatable structure to rotate such that the light is able to pass through the window when the window is aligned with respect to the light source and the image sensor, and wherein the optical fiber extends into the first non-rotatable housing structure, the optical fiber to transmit light through an optical window of the first non-rotatable housing structure.

16. The imaging-based measurement apparatus of claim 15, further comprising a second non-rotatable housing structure that comprises the image sensor, the rotatable rod separating the first and second non-rotatable housing structures, and rotatable the second non-rotatable housing structure comprising an optical window to receive the light passed through the optical window of the first non-rotatable housing structure and through the portion of the fluid.

* * * * *